(12) United States Patent
Lee et al.

(10) Patent No.: US 11,833,235 B2
(45) Date of Patent: Dec. 5, 2023

(54) COSMETIC AGENT COMPRISING INSOLUBLE SUBSTANCE AND METHOD FOR MANUFACTURING SAME

(71) Applicant: SUNJIN BEAUTY SCIENCE CO., LTD., Seoul (KR)

(72) Inventors: Sung Ho Lee, Ansan-si (KR); Se Yeon Hwang, Ansan-si (KR); Yeong Gi Kim, Ansan-si (KR)

(73) Assignee: SUNJIN BEAUTY SCIENCE CO., LTD., Ansan-si (KR)

( * ) Notice: Subject to any disclaimer, the term of this patent is extended or adjusted under 35 U.S.C. 154(b) by 0 days.

(21) Appl. No.: 16/978,865

(22) PCT Filed: Apr. 3, 2019

(86) PCT No.: PCT/KR2019/003917
§ 371 (c)(1),
(2) Date: Sep. 8, 2020

(87) PCT Pub. No.: WO2019/194560
PCT Pub. Date: Oct. 10, 2019

(65) Prior Publication Data
US 2021/0007949 A1    Jan. 14, 2021

(30) Foreign Application Priority Data

Apr. 3, 2018   (KR) .......... 10-2018-0038730
Apr. 3, 2018   (KR) .......... 10-2018-0038732

(51) Int. Cl.
| | | |
|---|---|---|
| *A61K 8/25* | (2006.01) | |
| *A61K 8/06* | (2006.01) | |
| *A61K 8/42* | (2006.01) | |
| *A61Q 19/00* | (2006.01) | |

(52) U.S. Cl.
CPC .......... *A61K 8/25* (2013.01); *A61K 8/06* (2013.01); *A61K 8/42* (2013.01); *A61Q 19/00* (2013.01); *A61K 2800/10* (2013.01); *A61K 2800/651* (2013.01)

(58) Field of Classification Search
None
See application file for complete search history.

(56) References Cited

U.S. PATENT DOCUMENTS

2020/0405597 A1\*   12/2020   Lee .................. A61K 8/06

FOREIGN PATENT DOCUMENTS

| KR | 10-2008-0065726 | 7/2008 |
| KR | 10-2010-0137386 | 12/2010 |
| KR | 10-2012-0120522 | 11/2012 |
| KR | 10-2016-0065658 | 6/2016 |
| KR | 10-2018-0023537 | 3/2018 |

OTHER PUBLICATIONS

English translation of WO2017/057873A1(2022).\*

\* cited by examiner

*Primary Examiner* — Patricia Duffy
*Assistant Examiner* — Garen Gotfredson
(74) *Attorney, Agent, or Firm* — LEX IP MEISTER, PLLC

(57) ABSTRACT

The present invention relates to a polyhedral complex, a cosmetic agent having the polyhedral complex formed therein, and a cosmetic composition comprising same, the polyhedral complex comprising: a thixotropic polyhedral structure formed of a plurality of flat-type substances; and a mixture of a functional substance and a solvent accommodated in the polyhedral structure. Furthermore, the present invention relates to a method for manufacturing the cosmetic agent, the method comprising: mixing the plurality of flat-type substances, the functional substance, and the solvent; and high-pressure spraying the mixture, and to a method for stabilizing the functional substance in the cosmetic agent.

3 Claims, 6 Drawing Sheets

COMPARATIVE EXAMPLE 1

COMPARATIVE EXAMPLE 2

COMPARATIVE EXAMPLE 3

COMPARATIVE EXAMPLE 1

COMPARATIVE EXAMPLE 2

COMPARATIVE EXAMPLE 3

COSMETIC AGENT COMPRISING INSOLUBLE SUBSTANCE AND METHOD FOR MANUFACTURING SAME

TECHNICAL FIELD

The present invention relates to a cosmetic agent including a poorly soluble material such as ceramide at a high concentration, and a cosmetic composition including the same. Even though the cosmetic agent and the cosmetic composition including the same of the present invention include the poorly soluble material at a high concentration, the cosmetic agent and the cosmetic composition have excellent stability so that a functional material is not precipitated, are easy to prepare, and have an excellent skin protection effect and excellent spreadability.

BACKGROUND ART

Various materials are used for imparting functionality to cosmetic agents.

However, among various materials for imparting functionality to cosmetic agents, there are many poorly insoluble materials. Specifically, materials including polyphenols such as amentoflavone, an ellagic acid, apigenin, berginin, diosmetin, univestin, resveratrol, isoflavone, and catechin; oily fatty acids such as a salicylic acid, an alpha lipoic acid, caffeine, tocopherol, a docosahexaenoic acid (DHA), an eicosapentaenoic acid (EPA), and a conjugated linolenic acid (CLA); sphingomyelin; sphingolipids such as ganglioside, cerebroside, ceramide, galactosyl ceramide, and xylosine ceramide; natural extracts including a ginkgo leaf extract, a red ginseng extract, and polyphenols; carotene or carotene derivatives; and retinol may be used in a cosmetic agent but are poorly soluble.

For example, when ceramide, which is a structural material of skin cells known to be useful to increase a barrier function of the bottom of the stratum corneum, is included in a cosmetic agent, there are excellent effects of reducing a skin inflammation and protecting a skin. Thus, attempts are being made to apply the ceramide, pseudoceramide, and a functional material having functions equivalent to those of the ceramide and the pseudoceramide in a cosmetic agent.

However, since the ceramide is poorly soluble in water, oil, or silicone oil, when the ceramide is applied to a cosmetic composition, stability of the ceramide in the cosmetic composition is decreased, and thus, a coagulation phenomenon occurs between the ceramides. Accordingly, the ceramide is precipitated as a crystal. Even when the precipitated crystal is applied to a skin, a desired effect cannot be achieved, and thus, it is difficult to apply the ceramide to the cosmetic composition.

In order to solve such a problem, in a water-based cosmetic agent, technology for combining liposome to a poorly soluble functional material such as ceramide to apply the resultant combination to the water-based cosmetic agent has been developed. However, in technologies applied to a water-based cosmetic agent, such as a method of combining liposome to a poorly soluble functional material, solubility and stability are lowered in an oil phase base, and thus, it has been difficult to add the poorly soluble functional material to an oil-based cosmetic at a high concentration.

Meanwhile, as compared with water-based cosmetic agents, oil-based cosmetic agents have many advantages because the oil-based cosmetic agents simultaneously form an oil film on a skin to inhibit moisture evaporation and maintain moisture to soften the skin. There is a lot of demand for oil-based cosmetic agents including poorly soluble materials at a high concentration, but technologies developed to date are not satisfactory. Therefore, there is a need to develop more advanced technology for oil-based cosmetic agent including a poorly soluble material at a high concentration.

DISCLOSURE

Technical Problem

The present invention is directed to providing a cosmetic agent and a cosmetic composition, in which, even when a poorly soluble functional material is included in an oil phase base or a silicone oil base at a high concentration, the functional material is not precipitated as a crystal, and which have fewer side effects to a human body, allow the functional material to easily penetrate into a skin to impart functionality at a high concentration and provide an excellent skin protection effect, are easy to prepare, and have excellent stability and spreadability, and a method of preparing the cosmetic agent.

In addition, the present invention is directed to providing a method of stabilizing a functional material in a cosmetic agent/cosmetic composition which is easily dispersed, has excellent stability and in which a poorly soluble functional material is included at a high concentration, the functional material is not precipitated as a crystal.

Technical Solution

The present invention provides a cosmetic agent including a plurality of plate-like materials, a functional material, and a solvent, wherein the plurality of plate-like materials form a polyhedral structure, and the functional material and the solvent are accommodated in the polyhedral structure to form a polyhedral complex.

The cosmetic agent may further include an emulsifier. In addition, the cosmetic agent may additionally include a fatty acid and/or cholesterol. Any materials commonly used in a cosmetic field may be used as the fatty acid and the cholesterol.

The plurality of plate-like materials may each have a surface having a lipophilic property and each include a hydroxy group at an edge thereof to form a polyhedral structure, in particular, a thixotropic polyhedral structure. In particular, the plurality of plate-like materials may be surface-treated with a quaternary ammonium salt having a lipophilic moiety.

A commercially available material may be used as the plate-like material may be. The plate-like material may be smectite clay, for example, hectorite or bentonite. Specifically, the hectorite may be disteardimonium hectorite or stearalkonium hectorite.

The functional material may be a skin tissue material or a precursor material, for example, ceramide and pseudoceramide. In the present invention, the functional material may be included in the cosmetic agent in a range of 0.001 wt % to 50 wt %, preferably in a range of 10 wt % or more, and more preferably in a range of 20 wt % or more.

In another aspect, the present invention provides a cosmetic composition including the cosmetic agent and additives that are acceptable in other cosmetics In still another aspect, the present invention provides a method of preparing a cosmetic agent.

The method includes (a) mixing a plurality of plate-like materials, a functional material, and a solvent, and (b) spraying the mixed product obtained in operation (a) at high pressure.

The plurality of plate-like materials each have a surface having a lipophilic property and each include a hydroxy group at a corner thereof In the cosmetic agent, the plurality of plate-like materials form a polyhedral structure.

The functional material and the solvent are accommodated in the polyhedral structure to form a polyhedral complex.

An emulsifier may be added and mixed in operation (a).

The spraying at high pressure may be performed at a pressure of 100 bar to 1,500 bar, preferably 500 bar to 1,000 bar, and more preferably 500 bar to 700 bar using a nozzle having a diameter of 1 µm to 50 µm and may be performed once or more, preferably 3 times to 10 times, and more preferably 3 times to 5 times.

The mixing (a) may be performed as a continuous mixing operation of mixing the functional material and the solvent, adding and mixing the plate-like materials, and then adding and mixing an emulsifier.

In yet another aspect, the present invention provides a method of stabilizing a functional material in a cosmetic agent, The method includes (a) mixing a plurality of plate-like materials, a functional material, and a solvent, and (b) spraying the mixed product obtained in operation (a) at high pressure.

The plurality of plate-like materials each have a surface having a lipophilic property.

The plurality of plate-like materials each include a hydroxy group at a corner thereof.

The functional material and the solvent are accommodated in a polyhedral structure made of the plurality of plate-like materials to form a polyhedral complex.

In yet another aspect, the present invention provides a polyhedral complex includes a thixotropic polyhedral structure made of a plurality of plate-like materials which each have a surface having a lipophilic property and each include a hydroxy group at a corner thereof, and a mixture of a ceramide and a solvent accommodated in the thixotropic polyhedral structure.

Advantageous Effects

The present invention provides a cosmetic agent in which, even when a poorly soluble functional material is included in an oil phase base or a silicone oil base at a high concentration, the functional material is not precipitated as a crystal, and which has fewer side effects to a human body, allows the functional material easily to penetrate into a skin to impart functionality at a high concentration and provide an excellent skin protection effect, is easy to prepare, and have excellent stability and spreadability, a method of preparing the same, and a cosmetic composition including the same.

In addition, the present invention provides a method of stabilizing a functional material in a cosmetic agent which is easily dispersed and has excellent stability and in which, even when a poorly soluble functional material is included at a high concentration, the functional material is not precipitated as a crystal.

The cosmetic agent/cosmetic composition of the present invention has advantages in that, even when a poorly soluble functional material is included at a high concentration, the functional material is not precipitated as a crystal, side effects to a human body are small, the functional material easily penetrates into a skin to impart functionality at a high concentration and provide an excellent skin protection effect, the preparation thereof is easy, and the stability and spreadability thereof are excellent.

BEST MODES OF THE INVENTION

Figure 1:
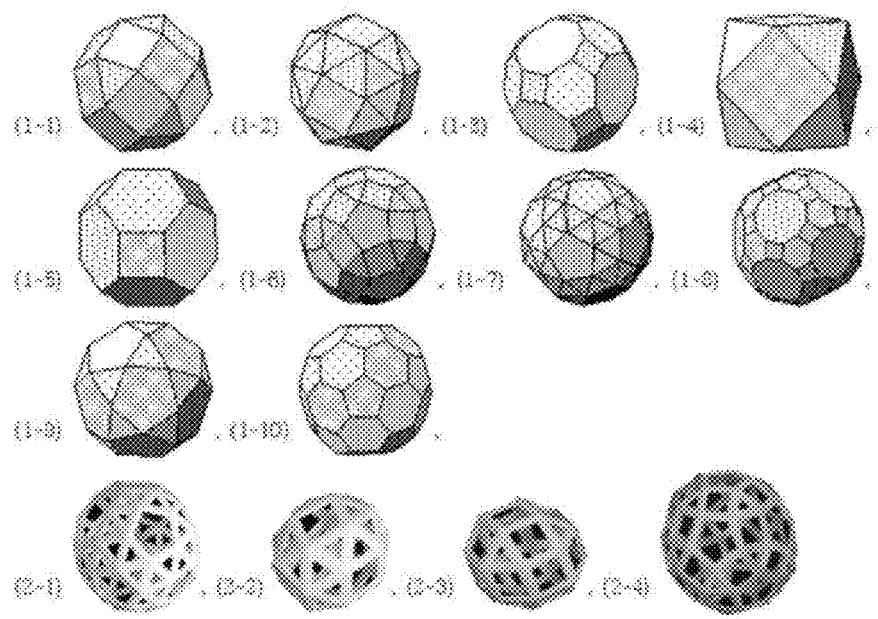
FIG. 1 shows three-dimensional schematic diagrams illustrating a polyhedral structure formed due to plate-like materials of the present invention forming partition walls through a card house arrangement and also illustrating a polyhedral composite in which a functional material and a solvent are accommodated in the polyhedral structure.

The present invention relates to a cosmetic agent including a plurality of plate-like materials, which each have a surface having a lipophilic property and each include a hydroxy group at a corner thereof, in a range of 1 wt % to 15 wt %, a functional material in a range of 0.001 wt % to 50 wt %, a solvent in a range of 20 wt % to 70 wt %, and an emulsifier in a range of 10 wt % to 60 wt %, wherein the plurality of plate-like materials form a polyhedral structure, and the functional material and the solvent are accommodated in the polyhedral structure to form a polyhedral complex.

The present invention provides a method of preparing a cosmetic agent, which includes (a) mixing a plurality of plate-like materials, which each have a surface having a lipophilic property and each include a hydroxy group at a corner thereof, a functional material, and a solvent, and (b) spraying the mixed product obtained in operation (a) once to 10 times at a high pressure of 100 bar to 1,500 bar, preferably 500 bar to 1,000 bar, and more preferably 500 bar to 700 bar, wherein, in the cosmetic agent, the plurality of plate-like materials form a polyhedral structure, and the functional material and the solvent are accommodated in the polyhedral structure to form a polyhedral complex.

The present invention provides a method of stabilizing a functional material in a cosmetic agent, which includes (a) mixing a plurality of plate-like materials, which each have a surface having a lipophilic property and each include a hydroxy group at a corner thereof, a functional material, and a solvent, and (b) spraying the mixed product obtained in operation (a) once to 10 times at a high pressure of 100 bar to 1,500 bar, preferably 500 bar to 1,000 bar, and more preferably 500 bar to 700 bar, wherein the functional material and the solvent are accommodated in a polyhedral structure formed of the plurality of plate-like materials to form a polyhedral complex.

Modes of the Invention

Hereinafter, the present invention will be described in detail so that those skilled in the art to which the present invention pertains can realize the present invention.

The present invention relates to a cosmetic agent including a plurality of plate-like materials, which each have a surface having a lipophilic property and each include a hydroxy group at a corner thereof, a functional material, and a solvent, wherein the plurality of plate-like materials form a polyhedral structure, and the functional material and the solvent are accommodated in the polyhedral structure to form a polyhedral complex.

The cosmetic agent may include the plurality of plate-like materials, which each have the surface having the lipophilic property and each include the hydroxy group at the corner thereof, in a range of 1 wt % to 15 wt %, the functional material in a range of 0.001 wt % to 50 wt %, the solvent in a range of 20 wt % to 70 wt %, and an emulsifier in a range of 10 wt % to 60 wt %. In this case, in the cosmetic agent, the functional material and the solvent may be accommodated in the polyhedral structure to form the polyhedral complex, thereby form the cosmetic agent which has excellent dispersibility and is stable.

A material, which is obtained by swelling and separating a smectite clay mineral into individual plate-like materials, and then, substituting surfaces of the plate-like materials with a lipophilic material, may be used as the plate-like material. The plate-like material may have the surface having the lipophilic property and may include the hydroxy group at the corner thereof.

The lipophilic material capable of imparting a lipophilic property to the plate-like material is not particularly limited as long as the lipophilic material may impart lipophilicity to a surface of the plate-like material. The lipophilic material may be a material including a $C_5$ to $C_{22}$ aliphatic alkyl residue. Specifically, the material including the $C_5$ to $C_{22}$ aliphatic alkyl residue may be a quaternary ammonium salt. For example, the quaternary ammonium salt may be a quaternary ammonium salt such as stearyl trimethyl ammonium chloride or dimethyl distearyl ammonium chloride.

The plate-like materials may form a thixotropic polyhedral structure having a card house arrangement, and corners between adjacent plate-like materials may be bonded through a bond having thixotropic properties, thereby forming the polyhedral structure. The bond may be released by an impact and then may be formed again to maintain the polyhedral structure.

Thicknesses and lengths of a major axis and a minor axis of the plate-like material may be arbitrarily selected. Specifically, the plate-like material may have a thickness of 0.0005 um and 0.005 um and a major axis of 0.5 um to 1.5 um. When the thickness and the major axis are within the ranges, it is particularly suitable for forming a polyhedral structure having excellent thixotropic properties and dispersibility.

The major axis of the plate-like material may have a length that is 0.3 to 3 times a maximum diameter of a mixture of the functional material and the solvent. In addition, the plate-like material may be a mixture of two or more different materials of which major axes have different lengths. For example, a material having a major axis of 0.8 um and a material having a major axis of 1.2 um may be mixed and used as the plate-like material. In this case, it is suitable for forming a polyhedral composite having a small pore size.

The shape of the surface of the plate-like material is not particularly limited, and the plate-like material may be a circular material, one of triangular to decagonal materials, or an atypical material or may be a mixture of two or more thereof. In addition, the polyhedral structure made of the plate-like materials may have a shape of 5-hedron to 500-hedron. For example, the polyhedral structure may be three-dimensionally one of polyhedral structures as shown in FIG. 1. In addition, the polyhedral structure may be a structure in which pores are blocked as shown in 1-1 to 1-10 of FIG. 1 or be a structure having pores as shown in 2-1 to 2-4 of FIG. 1. The polyhedral structure may be a structure of which corners are smooth and be a structure in which some of the plate-like materials protrude.

As specific examples of the plate-like material of the present invention, for example, there are attractive hectorite nanoplatelets (AHNPs) in which surfaces of hectorite nanoplatelets (HNPs) are substituted with dimethyl dihydrogenated tallow ammonium chloride (2Me2HT) and which include a hydroxy group at corners thereof. A commercially available material may be used. Specifically, stearalkonium hectorite sold under the trade name of Bentone 27V or disteardimonium hectorite sold under the trade name of Bentone 38V by Elementis Co. Ltd may be used.

In the cosmetic agent of the present invention, a polyhedral composite is formed in the form in which a functional material and a solvent are accommodated in a polyhedral structure made of a plurality of plate-like materials. Specifically, in the cosmetic agent of the present invention, while the plurality of plate-like materials surround the functional substrate dissolved in the solvent, corners between the plate-like materials are bonded through a bond having thixotropic properties to form a polyhedral structure having a card house arrangement. As a result, the functional material and the solvent are accommodated in the polyhedral structure to form the polyhedral complex.

The functional material and the solvent are not particularly limited as long as the functional material and the solvent may be used in a cosmetic agent, and when the solvent is in an oil phase, the functional material is a material that may be dissolved in the oil phase.

The functional material of the present invention may be a poorly soluble material. The poorly soluble material may be a skin tissue material or a precursor material and may be a material usable in a cosmetic field, which is at least one selected from polyphenols such as amentoflavone, an ellagic acid, apigenin, berginin, diosmetin, univestin, resveratrol, isoflavone, and catechin; oily fatty acids such as a salicylic acid, an alpha lipoic acid, caffeine, tocopherol, a docosahexaenoic acid (DHA), an eicosapentaenoic acid (EPA), and a conjugated linolenic acid (CLA); sphingomyelin; sphingolipids such as ganglioside, cerebroside, ceramide, galactosyl ceramide, and xylosine ceramide; natural extracts including a ginkgo leaf extract, a red ginseng extract, and polyphenols; carotene or carotene derivatives; and retinol.

Specifically, for example, the functional material may be ceramide or pseudoceramide. Ceramide EOP, ceramide NS, ceramide NP, ceramide AS, ceramide AP, and the like are known as types of ceramide. All of the ceramides may be used, but in particular, ceramide NP may be used. For example, ceramide NP (trade name: DS-Ceramide Y30 manufactured by Doosan Corporation) may be used.

Such a poorly soluble functional material is sufficient as long as the poorly soluble functional material may be accommodated in the polyhedral composite of the present invention.

In the present invention, the functional material may be included in the cosmetic agent in a range of 0.001 wt % to 50 wt %, preferably in a range of 10 wt % or more, and more preferably in a range of 20 wt % or more.

The solvent is not limited as long as the solvent is usable in ceramide and is commonly used in a cosmetic field. Oil or silicone oil to be described below may be used.

Specific example of oil may include at least one oil selected from the group consisting of coco-caprylate/caprate, caprylic/capric triglyceride, dicaprylyl carbonate, myristyl myristate, dicaprylyl ether, cetyl palmitate, octyldodecanol, hexyldecanol, hexyldecyl stearate, isostearyl isostearate, decyl oleate, hydrogenated vegetable oil, methylheptyl isostearate, nigella sativa seed oil, camellia oleifera seed oil, and *Passiflora incarnata* oil.

The silicone oil is not particularly limited as long as the silicone oil is a raw material that may be typically mixed into a cosmetic agent. Specifically, examples of the silicone oil may include phenyl trimethicone, cyclomethicone, dimethicone, and the like. In particular, phenyl trimethicone may be used. A commercially available product may be used as the silicone oil. For example, silicone oil sold by Shin-Etsu Chemical Co., Ltd maybe used.

The cosmetic agent including the polyhedral complex of the present invention may include the emulsifier, and in this case, a material commonly used in a cosmetic field may be used as the emulsifier. In particular, when a solvent of a polyhedral complex and a base of a cosmetic agent are different from each other, and when the polyhedral complex is prepared by adding an emulsifier, thereby forming the polyhedral complex having more excellent dispersibility and stability.

The emulsifier is not particularly limited as long as the emulsifier is a water-in-oil emulsifier usable in a cosmetic agent, and a content thereof may be arbitrarily adjusted.

As a specific example, the water-in-oil emulsifier may include at least one emulsifier selected from the group consisting of polyglyceryl-4 isostearate (HLB 5), polyglyceryl-3 polyricinoleate (HLB 4), polyglyceryl-3 diisostearate (HLB 55), polyglyceryl-4 oleate (HLB polyglyceryl-4 diisostearate/polyhydroxystearate/sebacate (HLB 5), diisostearoyl polyglyceryl-3 dimer dilinoleate (HLB 5), polyglyceryl-3 polyricinoleate (and) sorbitan isostearate (HLB 42), glyceryl laurate (HLB 52), sorbitan oleate (HLB 43), and sorbitan sesquioleate (HLB 37). For example, polyglyceryl-4 isostearate may be selected.

In addition, in the present invention, a water-in-silicone emulsifier may include partially crosslinked polyether-modified silicone, partially crosslinked polyglycerin-modified silicone, linear or branched polyoxyethylene-modified organopolysiloxane, liner or branched polyoxyethylene-polyoxypropylene-modified organopolysiloxane, linear or branched polyoxyethylene/alkyl co-modified organopolysiloxane, linear or branched polyoxyethylene-polyoxypropylene/alkyl co-modified organopolysiloxane, linear or branched polyglycerin-modified organopolysiloxane, or linear or branched polyglycerin/alkyl co-modified organopolysiloxane. As specific examples, there are emulsifiers sold under the trade names of KF-6011, KF-6013, KF-6043, KF-6028, KF-6038, KF-6048, KF-6100, KF-6104, KF-6105, and KF by Shin-Etsu Chemical Co., Ltd. More specifically, there may be lauryl PEG-9 polydimethylsiloxyethyl dimethicone with the trade name of KF-6038.

In addition, a fatty acid and/or cholesterol may be additionally included in the cosmetic agent of the present invention. Any materials commonly used in a cosmetic field may be used as the fatty acid and the cholesterol.

As described above, the present invention provides a polyhedral complex including a polyhedral structure which has a thixotropic property and is made of a plurality of plate-like materials (hectonite or bentonite), and a mixture of a functional material (ceramide) and a solvent which are accommodated in the polyhedral structure, and provides a cosmetic agent in which the polyhedral complex is formed.

Meanwhile, the present invention provides a cosmetic composition including the cosmetic agent and additives that are acceptable in other cosmetics.

The cosmetic composition of the present invention may include the cosmetic agent of the present invention in a range of 1 wt % to 10 wt %.

The cosmetic composition may be a basic cosmetic or color cosmetic. For example, the present invention is not limited to a skin lotion, lotion, cream, base make-up, eye make-up, lipstick, emulsion type, stick type, and crystal type formulations.

The cosmetic composition may include typical cosmetic additives. For example, the cosmetic composition may include antioxidants, preservatives, stabilizers, emollients, and perfumes. The antioxidants may include, for example, tocopherol or tocopherol acetate, in particular, tocopherol. The stabilizers may include, for example, magnesium sulfate, acrylate polymers, carbomers, starches, and xanthan gum. Suitable emollients may include paraffin and isoparaffin as well as an alkyl palmitate compound (for example, isopropyl palmitate). Buffer systems such as a citric acid and sodium citrate may also be optionally included. When the cosmetic composition of the present invention includes an oil phase base, the solvent used in the cosmetic agent and an oil phase of the oil phase base may be the same or different. In addition, when a cosmetic agent including a polyhedral complex is prepared using a solvent having higher solubility with respect to a functional material as compared with the oil phase of the oil phase base, the cosmetic agent may stably include the functional material at a higher concentration.

The oil phase in the cosmetic composition of the present invention may include any lipophilic components known in a cosmetic field. Above all, the lipophilic components include glycerides (monoglycerides, diglycerides, and triglycerides), fatty alcohols, fatty acid esters, hydrocarbons, silicone oils, and other synthetic oils and fats. Various vegetable oils and vegetable fats may be mentioned as suitable examples according to the invention, in particular, hydrogenated vegetable oils (such as olive oil or sunflower oil), long-chain hydrocarbons (such as paraffin, petroleum jelly, ceresin, ozokerite, or isohexadecane), or fatty acid esters (such as cetearyl isononanoate, ethylhexyl stearate, decyl oleate, isopropyl myristate, isopropyl palmitate, glyceryl stearate), and mixtures thereof. Suitable oil phases may be selected from the known materials by those skilled in the art, according to a desired product.

According to another aspect, the present invention provides a method of preparing a cosmetic agent, which includes (a) mixing a plurality of plate-like materials, which each have a surface having a lipophilic property and each include a hydroxy group at a corner thereof, a functional material, and a solvent, and (b) spraying the mixed product obtained in operation (a) at high pressure, wherein, in the cosmetic agent, the plurality of plate-like materials form a polyhedral structure, and the functional material and the solvent are accommodated in the polyhedral structure to form a polyhedral complex.

In the method of preparing a cosmetic agent, an emulsifier may be additionally mixed in operation (a). In addition, a fatty acid and/or cholesterol may be additionally included together with or separately from the emulsifier. Any materials commonly used in a cosmetic field may be used as the fatty acid and the cholesterol.

In the method of preparing a cosmetic agent of the present invention, the spraying at high pressure may be performed at a pressure of 100 bar to 1,500 bar, preferably 500 bar to 1,000 bar, and more preferably 500 bar to 700 bar using a nozzle having a diameter of 1 μm to 50 μm and may be performed once or more, preferably 3 times to 10 times, and more preferably 3 times to 5 times.

In the method of preparing a cosmetic agent of the present invention, the mixing (a) may be a continuous mixing operation of mixing the functional material and the solvent, adding and mixing the plate-like materials, and then adding and mixing the emulsifier.

In addition, in the present invention, when the functional material, the solvent, and the plurality of plate-like materials are sprayed at high pressure and mixed, a nano-dispersion high-pressure homogenizer or a microfluidizer (MF) may be used. By using the nozzle having a diameter of 1 μm to 50 μm, a mixed solution may be sprayed at a pressure of 100 bar to 1,500 bar, preferably 500 bar to 1,000 bar, and more preferably 500 bar to 700 bar using a nozzle having a diameter of 1 μm to 50 μm, and the spraying may be performed once or more, specifically, 3 times to 10 times. For example, the mixed solution be sprayed three times at a pressure of 700 bar.

When a conventional general mixer is used to perform mixing, it has been difficult to form the polyhedral composite of the present invention, in which the functional material and the solvent are accommodated in the polyhedral structure. However, when a cosmetic agent is prepared by spraying a mixture of a functional material, a solvent, a plurality of plate-like materials, and an optional emulsifier at high pressure using a nano-dispersion high-pressure homogenizer under conditions as described above, in the cosmetic agent, a polyhedral structure may be formed through a thixotropic bond, for example, a hydrogen bond between edges of the plurality of plate-like materials, and the functional material and the solvent may be accommodated in the polyhedral structure, thereby providing a cosmetic agent in which a functional material is not precipitated as in the present invention.

In addition, the present invention provides a method of stabilizing a functional material in a cosmetic agent, which includes (a) mixing a plurality of plate-like materials, which each have a surface having a lipophilic property and each include a hydroxy group at a corner thereof, a functional material, and a solvent, and (b) spraying the mixed product obtained in operation (a) at high pressure, wherein the functional material and the solvent are accommodated in a polyhedral structure made of the plurality of plate-like materials to form a polyhedral complex.

In the method of stabilizing a functional material of the present invention, a fatty acid and/or cholesterol may be additionally included in operation (a) to further stabilize the functional material.

Hereinafter, specific Examples of the present invention will be described. However, the present invention may be implemented in various forms, and the scope of the present invention should not be interpreted as being limited to Examples described below. In addition, simple modifications or variations of the present invention can be easily implemented by those of ordinary skill in the art based on the description of the specification of the present invention and the common sense in the art, and all of the modifications or variations fall within the scope of the present invention.

Preparation Example 1

Preparation Example of Cosmetic Agent with Polyhedral Complex Accommodating Ceramide The following raw materials and contents were used to prepare a cosmetic agent with a polyhedral composite.

TABLE 1

| Raw material | Content (wt %) | Trade name |
| --- | --- | --- |
| caprylic/capric triglyceride (CCTG) | 25 | bergabest mct oil 60/40 |
| ceramide NP | 20 | DS-Ceramide Y30 |
| disteardimonium hectorite | 15 | Bentone 38V |
| polyglyceryl-4 isostearate | 40 | Isolan G134 |

A solution was prepared by mixing ceramide NP and CCTG in an agi-mixer at a temperature of 90° C. Disteadimonium hectorite was added to the solution and mixed at a speed of 400 rpm to 500 rpm in the agi-mixer. Polyglyceryl-4 isostearate was further added to the resultant mixture and mixed at a speed of 400 rpm to 500 rpm in the agi-mixer. The mixture was sprayed three times at a high pressure of 700 bar using a microfluidizer (MF) to prepare the cosmetic agent with the polyhedral composite.

Figure 2:
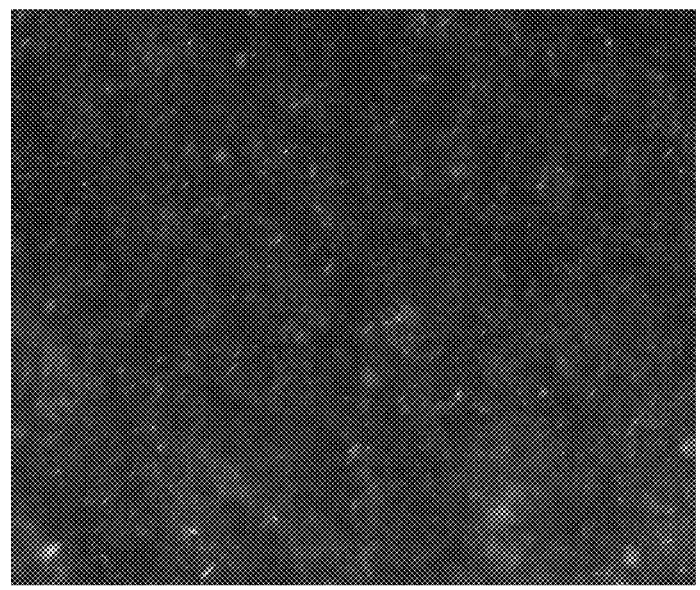
FIG. 2 is an image obtained by photographing a cosmetic agent of Preparation Example 1 using a polarizing microscope (with model name: BX53-P and magnification of 400 times) manufactured by Olympus Company.
Figure 3:
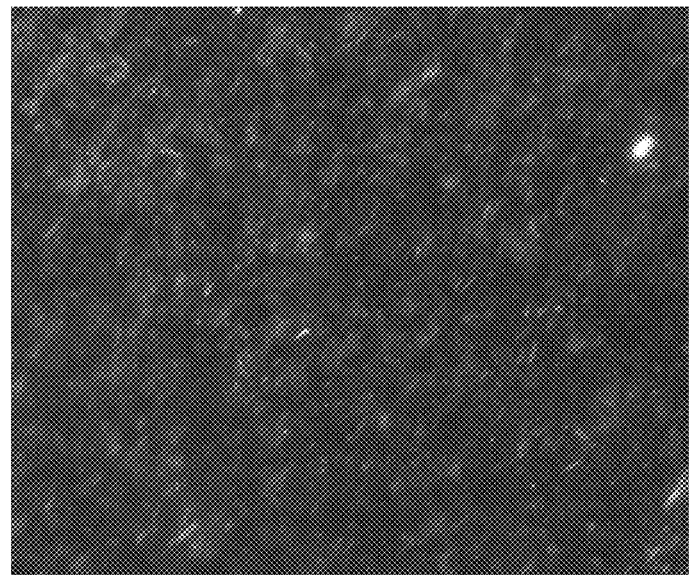
FIG. 3 is an image obtained by photographing the cosmetic agent of Preparation Example 1 using a polarizing microscope (with model name: BX53-P and magnification of 400 times) manufactured by Olympus Company after the cosmetic agent is left at a temperature of 45° C. for five weeks.
Figure 4:
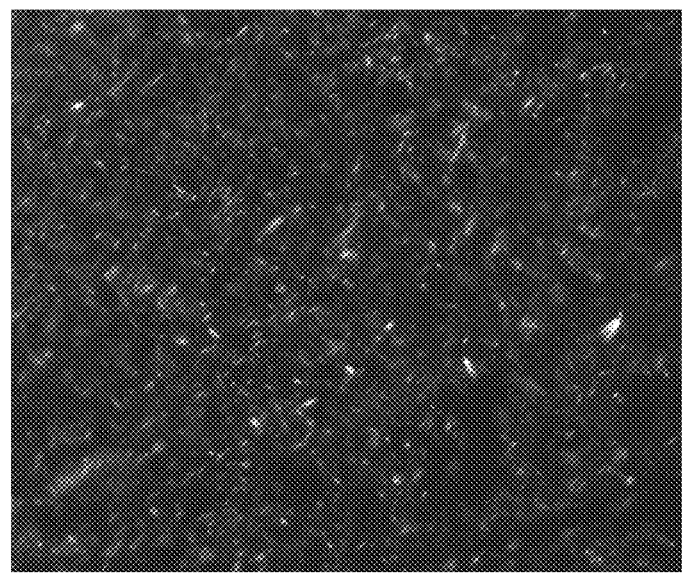
FIG. 4 is an image obtained by photographing the cosmetic agent of Preparation Example 1 using a polarizing microscope (with model name: BX53-P and magnification of 400 times) manufactured by Olympus Company after the cosmetic agent is left at a temperature of 0° C. to 5° C. for five weeks.

An image obtained by photographing the cosmetic agent using a polarizing microscope (with model name: BX53-P and magnification of 400 times) manufactured by Olympus Company is shown in FIG. 2. An image obtained by photographing the cosmetic agent after being left at a temperature of 45° C. for five weeks is shown in FIG. 3. In addition, an image obtained by photographing the cosmetic after being left at a temperature of 0° C. to 45° C. for five weeks is shown in FIG. 4. It can be seen from a size of a ceramide crystal that the ceramide crystal is hardly grown.

Preparation Example 2

Preparation Example of Cosmetic Agent with Polyhedral Complex Accommodating Ceramide The following raw materials and contents were used to prepare a cosmetic agent with a polyhedral composite.

TABLE 2

| Raw material | Content (wt %) | Trade name |
|---|---|---|
| caprylic/capric triglyceride (CCTG) | 25 | bergabest mct oil 60/40 |
| ceramide NP | 20 | DS-Ceramide Y30 |
| stearalkonium hectorite | 15 | Bentone 27V |
| polyglyceryl-4 isostearate | 40 | Isolan G134 |

A solution was prepared by heating ceramide NP and CCTG to a temperature of 90° C. in an agi-mixer. Stearalkonium hectorite was added to the solution and mixed at a speed of 400 rpm to 500 rpm in the agi-mixer. Polyglyceryl-4 isostearate was further added to the resultant mixture and mixed at a speed of 400 rpm to 500 rpm in the agi-mixer. The mixture was sprayed three times at a high pressure of 700 bar using a microfluidizer (MF) to prepare the cosmetic agent with the polyhedral composite.

Preparation Example 3

Preparation Example of Cosmetic Agent with Polyhedral Complex Accommodating Ceramide

TABLE 3

| Raw material | Content (wt %) | Trade name |
|---|---|---|
| phenyl trimethicone | 25 | DC556 |
| NP | 20 | DS-Ceramide Y30 |
| disteardimonium hectorite | 15 | Bentone 38V |
| lauryl PEG-9 polydimethylsiloxyethyl dimethicone | 40 | KF-6038 |

A solution was prepared by heating ceramide NP and phenyl trimethicone to a temperature of 90° C. in an agi-mixer. Disteadimonium hectorite was added to the solution and mixed at a speed of 400 rpm to 500 rpm in the agi-mixer. Lauryl PEG-9 polydimethylsiloxyethyl dimethicone was further added to the resultant mixture and mixed at a speed of 400 rpm to 500 rpm in the agi-mixer. The mixture was sprayed three times at a high pressure of 700 bar using a microfluidizer (MF) to prepare the cosmetic agent with the polyhedral composite.

Figure 5:
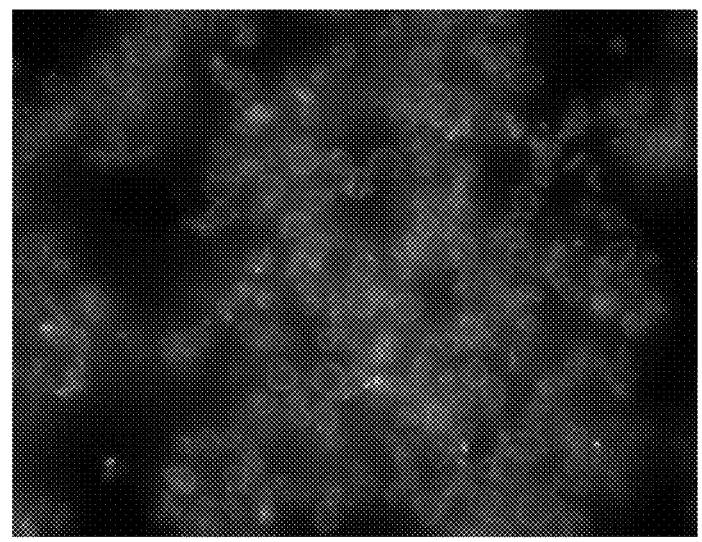
FIG. 5 is an image obtained by photographing a polyhedral complex in which ceramide NP and a solvent present in a cosmetic agent of Preparation Example 3 are accommodated in a hectorite polyhedral structure and obtained by photographing the polyhedral complex formed by using hectorite including a fluorescently labeled hydroxy group as a plate-like material.

In order to confirm a shape of the polyhedral composite in the cosmetic agent, an image obtained by fluorescently labeling and photographing a hydroxy group of a plate-like material is shown in FIG. 5. It can be confirmed through FIG. 5 that a polyhedral composite having a polygonal shape is formed.

Preparation Example 4

Preparation Example of Cosmetic Composition Including Cosmetic Agent of Preparation Example 2

The cosmetic agent of Preparation Example 2 and the components in Table below were emulsified at a speed of 1,200 rpm at room temperature for 5 minutes and mixed to prepare a cream.

TABLE 4

| Phase | Trade name | INCI | Content (wt %) |
|---|---|---|---|
| A |  | Cosmetic agent with polyhedral complex made of ceramide NP/CCTG/polyglyceryl-4 isostearate/disteardimonium hectorite (Example 2) | 2.5 |
|  | Isolan GI34 | polyglyceryl-4 isostearate | 1 |
|  | Cetiol C5C | coco-caprylate/caprate | 10 |
| B | water | water | 80.6 |
|  | NaCl | sodium chloride | 0.5 |
|  | glycerin | glycerin | 3 |
|  | 1,3-propandiol | propandiol | 1.7 |
|  | 1,2-hexanediol | hexanediol | 0.7 |

Figure 6:
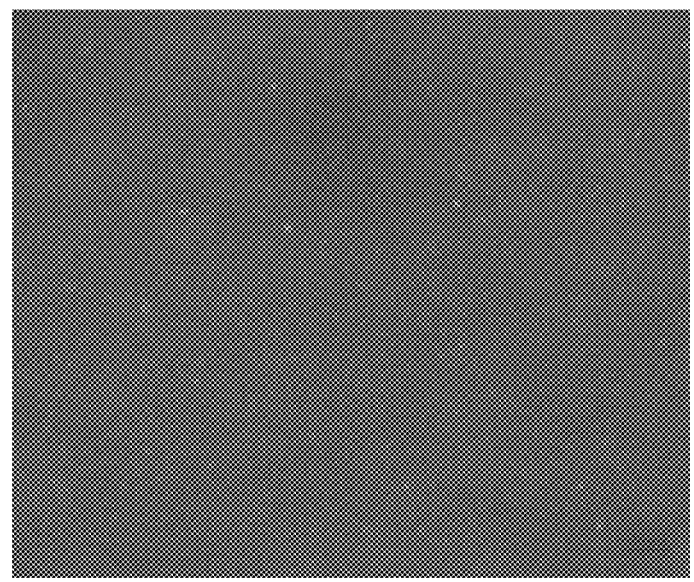
FIG. 6 is an image obtained by photographing a cosmetic composition of Preparation Example 4 using a polarizing microscope (with model name: BX53-P and magnification of 400 times) manufactured by Olympus Company.
Figure 7:
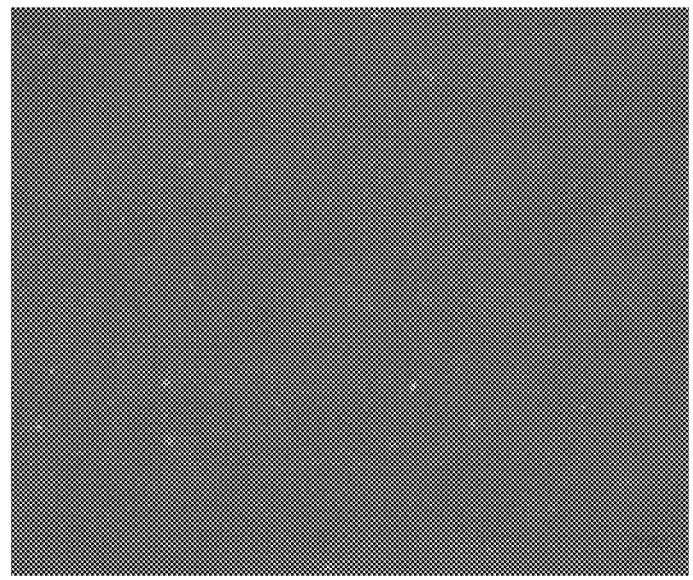
FIG. 7 is an image obtained by photographing the cosmetic composition of Preparation Example 4 using a polarizing microscope (with model name: BX53-P and magnification of 400 times) manufactured by Olympus Company after the cosmetic composition is left at room temperature for five weeks.
Figure 8:
FIG. 8 is an image obtained by photographing the cosmetic composition of Preparation Example 4 using a polarizing microscope (with model name: BX53-P and magnification of 400 times) manufactured by Olympus Company after the cosmetic agent is left at room temperature for five weeks and is additionally left at a temperature of 0° C. to 5° C. for one week.

An image obtained by photographing a cosmetic composition using a polarizing microscope (with model name: BX53-P and magnification of 400 times) manufactured by Olympus Company is shown in FIG. 6. An image obtained by photographing a cosmetic composition after being left at room temperature for five weeks is shown in FIG. 7. An image obtained by photographing a cosmetic composition after being additionally left at a temperature of 0° C. to 5° C. for one week is shown in FIG. 8. It can be seen from a size of a ceramide crystal that the ceramide crystal is hardly grown.

Comparative Example 1

In order to verify the excellence of the cosmetic agents including the polyhedral composite of the preparation examples of the present invention, Comparative Examples 1 to 3 were prepared using the components shown in Table below.

In Comparative Example 1, ceramide, an emulsifier, and other components were used and mixed as in a typical preparing method.

In Comparative Example 2, disteardimonium hectorite and ceramide were used together, but unlike the present invention, Comparative Example 2 was prepared without performing high-pressure spraying using an MF.

Comparative Example 3, which is a cosmetic composition including a cosmetic agent in which a polyhedral composite is formed (wherein MF treatment is performed by adding hectorite without adding ceramide), was set as a control group in order to confirm how hectorite is viewed through a polarizing microscope. As can be seen from the control group, since hectorite is not visible through the polarizing microscope, it can be confirmed that white crystals shown in the images of other Comparative Examples are ceramide crystals.

TABLE 5

| Phase | | INCI | Example 4 | Comparative Example 1 | Comparative Example 2 | Comparative Example 3 |
|---|---|---|---|---|---|---|
| A | Example 2 | Cosmetic agent with polyhedral complex made of ceramide NP/CCTG/polyglyceryl-4 isostearate/disteardimonium hectorite | 2.5 | — | — | — |
| | | Cosmetic agent with polyhedral complex made of cetiol C5C/polyglyceryl-4 isostearate/disteardimonium hectorite | — | — | — | 5 |
| | ceramide NP | ceramide NP | — | 0.5 | 0.5 | — |
| | Isolan GI34 | polyglyceryl-4 isostearate | 1 | 2 | 2 | — |
| | Bentone 38V | disteardimonium hectorite | — | — | 0.38 | — |
| | Cetiol C5C | coco-caprylate/caprate | 10 | 11 | 10.62 | 8.5 |
| B | water | water | 80.6 | 80.6 | 80.6 | 80.6 |
| | NaCl | sodium chloride | 0.5 | 0.5 | 0.5 | 0.5 |
| | glycerin | glycerin | 3 | 3 | 3 | 3 |
| | 1,3-propandiol | propandiol | 1.7 | 1.7 | 1.7 | 1.7 |
| | 1,2-hexanediol | hexanediol | 0.7 | 0.7 | 0.7 | 0.7 |

Figure 9:
FIG. 9 shows images obtained by photographing compositions of Comparative Examples 1 to 3 using a polarizing microscope (with model name: BX53-P and magnification of 400 times) manufactured by Olympus Company.
Figure 9:
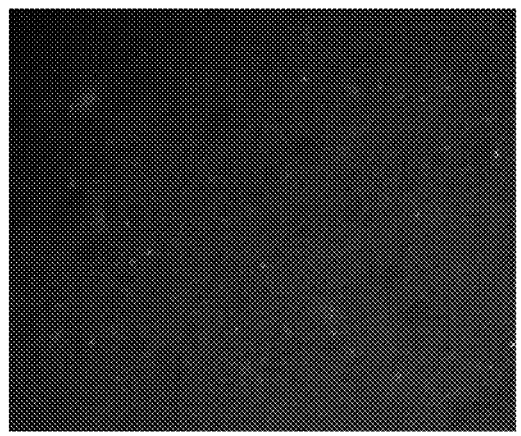
Figure 9:
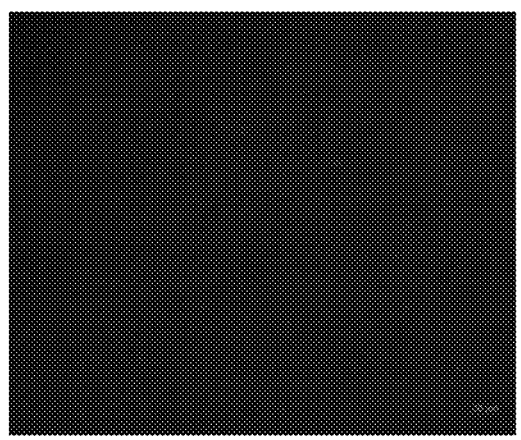

Images obtained by photographing Comparative Examples 1 to 3 using a polarizing microscope (with model name: BX53-P and magnification of 400 times) manufactured by Olympus Company are shown in FIG. 9, and images by photographing Comparative Examples 1 to 3 after being left at room temperature for five weeks are shown in FIG. 10.

Figure 10:
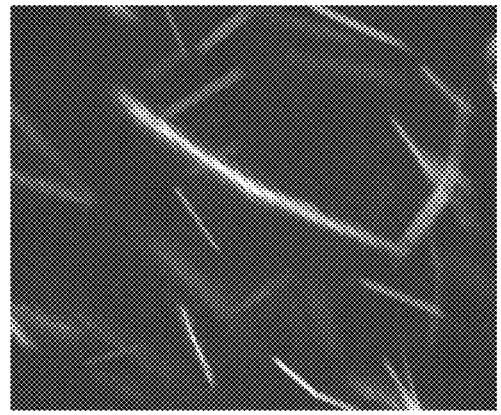
FIG. 10 shows images obtained by photographing the compositions of Comparative Examples 1 to 3 using a polarizing microscope (with model name: BX53-P and magnification of 400 times) manufactured by Olympus Company after the compositions are left at room temperature for five weeks.
Figure 10:
Figure 10:
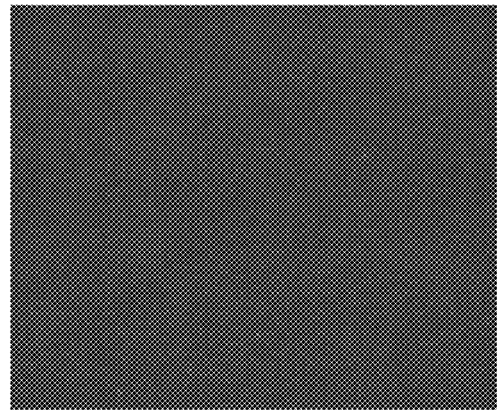

As can be seen in FIG. 10, in Comparative Examples 1 and 2, ceramide crystals were observed. In Comparative Example 3, since ceramide was not added, crystal formation was not observed. It can be seen from Comparative Example 3 that the ceramide crystals were observed in Comparative Examples 1 and 2.

When the images of Comparative Examples 1 and 2 are compared with the image of Preparation Example 4, it can be confirmed that, in the cosmetic composition of Preparation Example 4, ceramide has not been observed as crystals. Therefore, it can be confirmed that the cosmetic agent including the polyhedral composite of the present invention may stably include a functional material at a high concentration.

INDUSTRIAL APPLICABILITY

The present invention relates to a cosmetic agent including a poorly soluble material such as ceramide at a high concentration, a method of preparing the same, and a cosmetic composition including the same.

Even though the cosmetic agent and the cosmetic composition including the same of the present invention include the poorly soluble material at a high concentration, the cosmetic agent and the cosmetic composition have excellent stability so that a functional material is not precipitated, are easy to prepare, and have an excellent skin protection effect and excellent spreadability.

The present invention can be used in industry of a cosmetic field.

The invention claimed is:
1. A cosmetic agent comprising:
a plurality of plate-like materials, each having a surface having a lipophilic property and each including a hydroxy group at a corner thereof;
a functional material;
a solvent; and
an emulsifier,
wherein the plurality of plate-like materials is included in an amount of 1 to 15 wt %,
wherein the functional material is included in an amount of 0.001 to 50 wt %,
wherein the solvent is included in an amount of 20 to 70 wt %,
wherein the emulsifier is included in an amount of 10 to 60 wt %,
wherein each of the plurality of plate-like materials is disteardimonium hectorite or stearalkonium hectorite,
wherein a length of a major axis of each of the plurality of plate-like materials is 0.5 to 1.5 μm,
wherein the functional material is ceramide,
wherein the emulsifier is selected from the group consisting of polyglyceryl-4 isostearate, polyglyceryl-3 polyricinoleate, polyglyceryl-3 diisostearate, polyglyceryl-4 oleate, polyglyceryl-4 diisostearate/polyhydroxystearate/sebacate, diisostearoyl polyglyceryl-3 dimer dilinoleate, polyglyceryl-3 polyricinoleate, sorbitan isostearate, glyceryl laurate, sorbitan oleate, and sorbitan sesquioleate,
wherein the solvent is capable of dissolving ceramide,
wherein the plurality of plate-like materials form a polyhedral structure, and the functional material and the solvent are accommodated in the polyhedral structure to form a polyhedral complex, and
wherein the polyhedral structure is a thixotropic polyhedral structure.

2. The cosmetic agent of claim 1, wherein the functional material is included in a range of 20 wt % to 50 wt %.

3. A cosmetic composition comprising the cosmetic agent of claim 1.

* * * * *